United States Patent
Hohman et al.

(10) Patent No.: US 7,902,819 B2
(45) Date of Patent: Mar. 8, 2011

(54) RIVET ROTATING EDDY CURRENT PROBE

(75) Inventors: Edward Hohman, Mansfield, TX (US);
Dennis Roach, Albuquerque, NM (US);
Rirk Rackow, Albuquerque, NM (US);
Phil Walkington, Albuquerque, NM (US)

(73) Assignee: Textron Innovations, Inc., Providence, RI (US)

( * ) Notice: Subject to any disclaimer, the term of this patent is extended or adjusted under 35 U.S.C. 154(b) by 558 days.

(21) Appl. No.: 11/664,665

(22) PCT Filed: Oct. 7, 2005

(86) PCT No.: PCT/US2005/036070
§ 371 (c)(1),
(2), (4) Date: Dec. 19, 2007

(87) PCT Pub. No.: WO2007/015705
PCT Pub. Date: Feb. 8, 2007

(65) Prior Publication Data
US 2008/0211493 A1    Sep. 4, 2008

Related U.S. Application Data

(60) Provisional application No. 60/617,311, filed on Oct. 8, 2004.

(51) Int. Cl.
*G01N 27/82* (2006.01)
*G01R 33/12* (2006.01)

(52) U.S. Cl. .................. 324/240; 324/242; 324/228

(58) Field of Classification Search .............. 324/222,
324/223, 228, 232, 234, 235, 236, 237, 238,
324/239, 230, 240, 241, 242, 243, 262
See application file for complete search history.

(56) References Cited

U.S. PATENT DOCUMENTS

| 5,648,721 | A | 7/1997 | Wincheski et al. |
| 7,301,335 | B2 * | 11/2007 | Sun et al. ................ 324/240 |
| 7,352,176 | B1 * | 4/2008 | Roach et al. ............. 324/240 |
| 2004/0051525 | A1 | 3/2004 | Hatcher et al. |

OTHER PUBLICATIONS

Canadian Office Action dated Jul. 6, 2009 from CA Application 2,580,278.
Response dated Dec. 31, 2009 from CA Application 2,580,278.
Chinese First Office dated May 25, 2009 from CA Application 2005800334800.
Response dated Jun. 26, 2009 from CN Application 2005800334800.
Chinese Second Office Action dated Dec. 11, 2009 from CN Application 2005800334800.
European Search Report dated Dec. 18, 2009 from EP Application 05858442.6.
U.S. Appl. No. 11/502,085, filed Aug. 10, 2006.
European Office Action dated Feb. 8, 2010 from EP Application 05858442.6.

* cited by examiner

*Primary Examiner* — Kenneth J Whittington
(74) *Attorney, Agent, or Firm* — James E. Walton; Richard G. Eldredge

(57) ABSTRACT

An eddy current probe adapted for detecting cracks in material directly beneath a raised-head fastener is disclosed. The probe comprises an eddy current coil and a support for carrying the coil in an orientation suitable for introducing eddy currents into material directly beneath a raised-head fastener.

19 Claims, 3 Drawing Sheets

RIVET ROTATING EDDY CURRENT PROBE

CROSS REFERENCE TO RELATED APPLICATIONS

This application is a Non-provisional Application of U.S. Provisional Application No. 60/617,311 filed on 8 Oct. 2004, titled "Rivet Rotating Probe," and is a U.S. National-stage application of International Application PCT/US2005/036070, filed on 7 Oct. 2005, titled "Rivet Rotating Probe".

TECHNICAL FIELD

The present invention relates in general to the field of non-destructive evaluation. In particular, the present invention relates to eddy current probes.

DESCRIPTION OF THE PRIOR ART

The outer skin of many aircraft comprise overlapping metal sheets joined together by inserting fasteners through overlapping portions of the metal sheets. A common problem related to using overlapping metal sheets is the undesirable existence and/or formation of cracks within the metal sheets and/or the fasteners which hold the sheets together. The cracks may exist in the sheets and/or fasteners as initially produced or the cracks may form after production. The cracks which form in the metal sheets and/or fasteners after initial production are commonly categorized as fatigue cracks caused by highly repetitious cyclic deformation of the metal sheets and/or fasteners. Since any crack in the metal sheets and/or fasteners may lead to catastrophic failure of the aircraft skin and subsequently a crash of the aircraft, detection of any crack is of the utmost importance.

One method well known and often used for detecting cracks in the metal sheets of an aircraft outer skin is to move a sliding eddy current probe along the surface of the metal sheet. A sliding eddy current probe typically comprises an electrical coil oriented parallel to a sliding surface of the sliding probe where the sliding surface is the surface placed in contact with the metal sheet. As the sliding eddy current probe passes over a crack, the presence of a crack is typically indicated by the presence of a crack signature viewable on a display screen of a connected probe controller. Cracks of different sizes, geometries, and locations often present crack signatures of different shapes, intensities, and/or amplitudes on the display screen. Further, a particular crack may present a variety of crack signatures depending upon a number of probe operating variables including the frequency at which the probe controller excites the electrical coil, the amplitude of the electrical signal transmitted to the probe from the probe controller, the geometry of the movements made with the probe along the surface of the metal sheet, and the speed with which the probe is manipulated. The sliding eddy current probe may be well suited for detecting some cracks located both, directly below the probe and in the metal sheet actually in contact with the probe; however, there are many scenarios where sliding eddy current probes do not offer adequate crack detection.

In helicopter construction, it is common practice to overlap metal sheets and join them together by inserting the raised-head fasteners through overlapping portions of the metal sheets. The raised-head fasteners are typically rivets comprising aerodynamic heads with smooth finishes. It is also common for the raised-head fasteners to be located substantially close together when used for securing the metal sheets of helicopter outer skins. Also, while the sliding eddy current probe may suitably detect cracks oriented in a manner aligned lengthwise with the direction of the lap joint, the sliding eddy current probe performs poorly in detecting cracks oriented transverse to the direction of the lap joint due to eddy current edge effects. Finally, the sliding eddy current probe is not well suited for detecting cracks where the sizes, geometries, and locations of a plurality of cracks may unfortunately be such that the probe response to the plurality of cracks results in no recognizable crack signature being displayed due to crack signature cancellation effects.

Although sliding eddy current probes are able to detect some cracks, many shortcomings remain.

SUMMARY OF THE INVENTION

There is a need for crack detection apparatus capable of detecting cracks beneath the head of a raised-head fastener.

Therefore, it is an object of the present invention to provide an eddy current probe having features suitable for detecting cracks beneath the head of a raised-head fastener.

This object is achieved by providing an eddy current probe comprising an eddy current coil and a support means for orienting the coil such that the eddy currents created by the coil are directed into the area of material beneath the head of a raised-head fastener.

The present invention provides significant advantages, including providing an eddy current probe that can: (1) detect cracks in metal sheets having closely located raised-head fasteners or raised-head fasteners in a closely located staggered pattern, (2) detect cracks located in metal sheets directly below the head of a raised-head fastener, (3) detect cracks in the head of a raised-head fastener, and (4) detect cracks which would otherwise go undetected by typical sliding probes due to crack signature cancellation and/or edge effects.

Other objects and advantages will become apparent from the detailed description that follows.

DESCRIPTION OF THE DRAWINGS

For a more complete understanding of the present invention, including its features and advantages, reference is now made to the detailed description of the invention taken in conjunction with the accompanying drawings in which like numerals identify like parts, and in which.

DESCRIPTION OF THE PREFERRED EMBODIMENT

Figure 1:
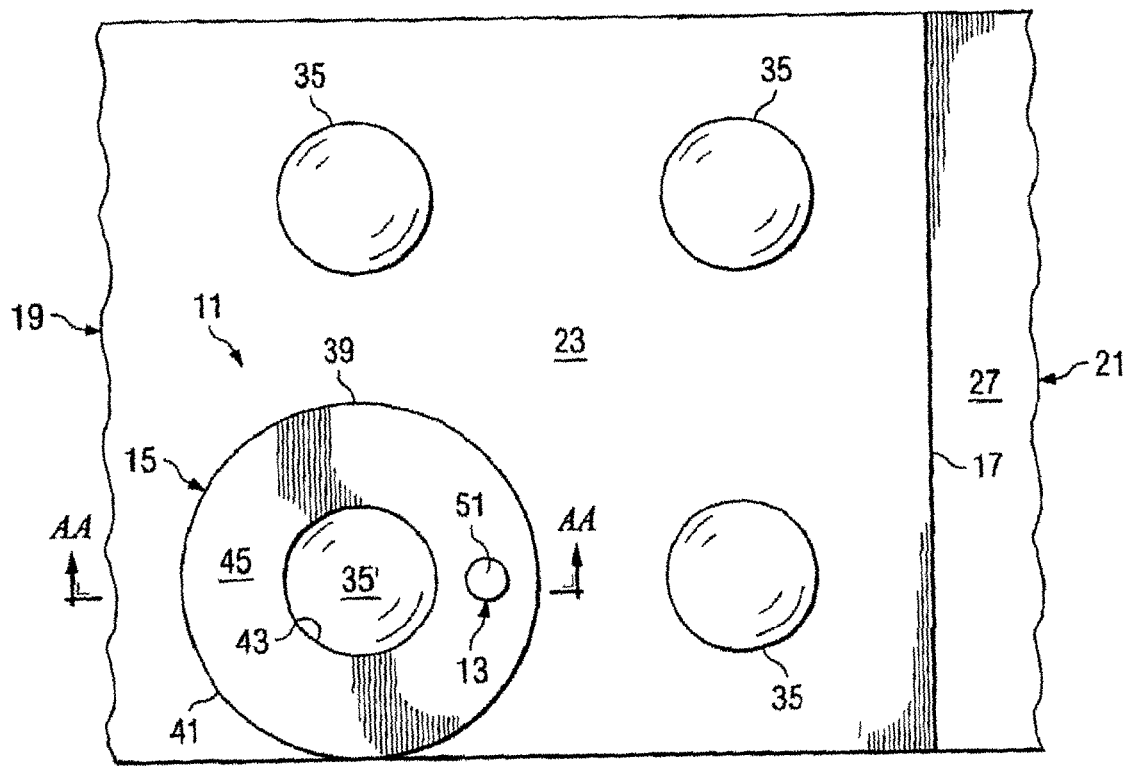
FIG. 1 is a top view of a probe according to the present invention.
Figure 2:
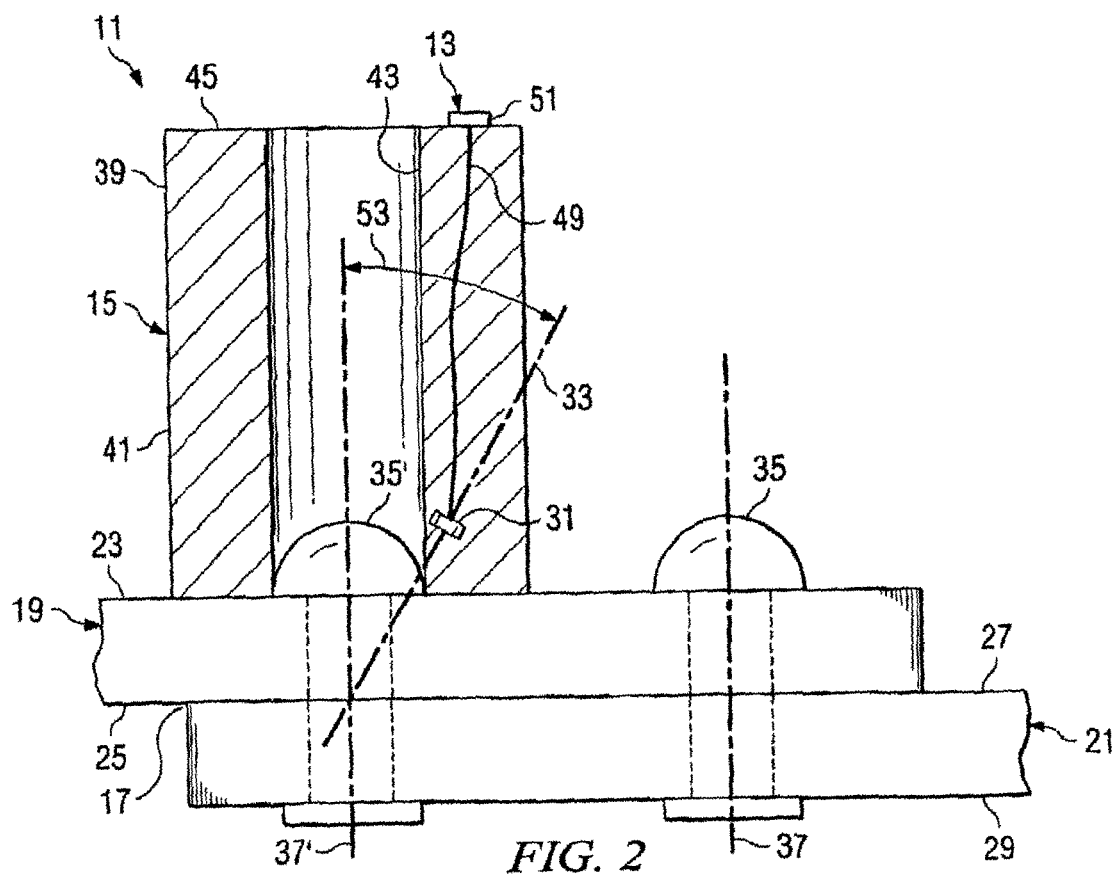
FIG. 2 is a sectional side view of the probe of FIG. 1.
Figure 3:
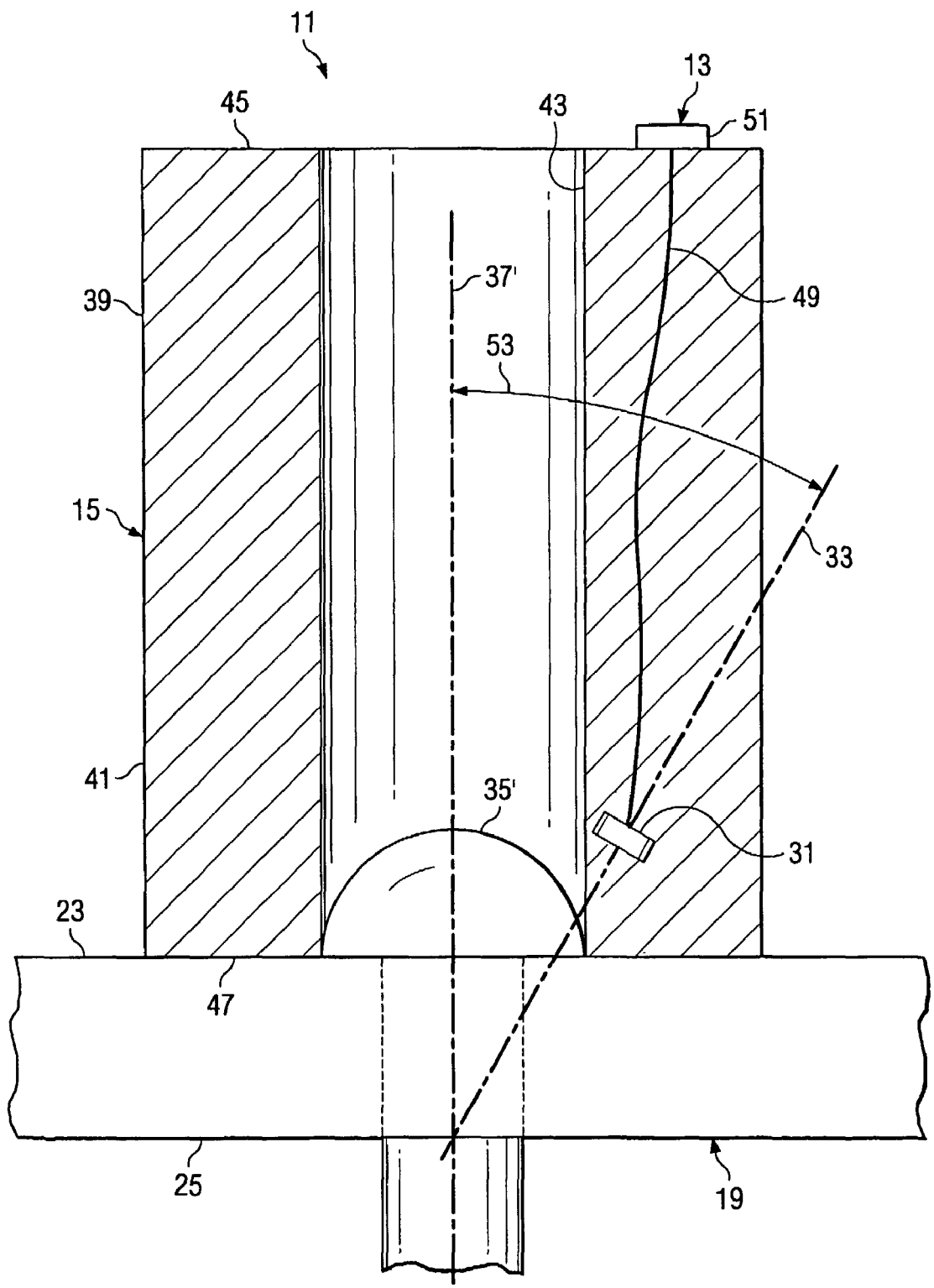
FIG. 3 is an enlarged sectional side view the probe of FIG. 1.

Referring now to FIGS. 1-3 in the drawings, an embodiment of the probe of the present invention is illustrated. FIG. 1 is a top view. FIG. 2 is a side view. FIG. 3 is an enlarged side view. Probe 11 comprises an eddy current coil system 13 and a support means 15 for supporting coil system 13. FIGS. 1 and 2 display sectional views of probe 11 as taken at cutting line AA of FIG. 1 and viewed in the direction indicated by the arrows attached to cutting line AA. For clarity and readability, only support means 15 is cross-hatched in FIG. 2. Probe 11 is situated atop a joint 17 joining an upper sheet 19 and a lower sheet 21. Sheets 19,21 are constructed of aluminum, but may alternatively be constructed of any other metal composition. Upper sheet 19 comprises an upper sheet top surface 23 and an upper sheet bottom surface 25. Lower sheet 21 comprises a lower sheet top surface 27 and a lower sheet bottom surface 29.

Eddy current coil system 13 comprises a disc-shaped coil 31 having a coil centerline 33 most clearly shown in FIG. 3. Upper sheet 19 and lower sheet 21 are joined together with raised-head fasteners 35 such that upper sheet bottom surface 25 is in substantial contact with lower sheet top surface 27. Raised-head fasteners 35 are constructed of aluminum, but may alternatively be constructed of any other metal composition. Raised-head fasteners 35 each have a fastener centerline 37. Fastener centerlines 37 are substantially orthogonal to upper sheet top surface 23. It will be appreciated that in some cases sheets 19,21 may be bent to form a contoured outer skin. Where sheets 19,21 are bent (not shown), fastener centerline 37 may not be substantially orthogonal to the entire upper sheet top surface 23 but rather substantially orthogonal to a smaller area of upper sheet top surface 23.

Support means 15 is a tubular member 39 having a substantially annular cross-section and having an outer wall 41, an inner wall 43, a top face 45, and a bottom face 47. The diameter of inner wall 43 is selected to substantially match the diameter of the head of fasteners 35 while providing proper tolerances for allowing rotation of probe 11 about fastener centerline 37 and/or along the perimeter of the head of fastener 35 while bottom face 47 of member 39 remains in contact with upper sheet top surface 23. Member 39 accepts fastener 35' within the inner void space of member 39 while bottom face 47 of member 39 remains in contact with upper sheet top surface 23.

Coil system 13 further comprises an electrical conductor 49 for connecting coil 31 to a modular electrical connector 51. Conductor 49 is substantially disposed between inner wall 43 and outer wall 41. Connector 51 is a "microdot" connector commonly used for connecting to a standard eddy current inspection unit (not shown). Connector 33 is located on top face 45. While typical eddy current probes are designed such that the centerline of a typical disc-shaped coil is oriented substantially orthogonal to the top surface of a sheet being inspected, coil 31 is oriented such that coil centerline 33 rests at an angle 53 of about 23 degrees from fastener centerline 37' as most clearly shown in FIG. 3. It will be appreciated that in other embodiments of the present invention, angle 53 may be a value different from 23 degrees. Coil 31 is substantially disposed between inner wall 43 and outer wall 41. Further, coil 31 is located such that while bottom face 47 of member 39 remains in contact with upper sheet top surface 23, eddy currents caused by coil 31 penetrate not only upper sheet 19 but also through the edge of the head of the fastener.

It will be appreciated that while coil 31 is described as an absolute single turn type coil, coil 31 could be replaced in alternative embodiments of the present invention by (1) multiple winding coils such as differential coil units, (2) multiple coil configurations such as reflection coil units, or (3) any other suitable eddy current coil configuration suitable for introducing eddy currents beneath the head of the fastener. It will also be understood that additional and/or different conductors 49 and connectors 51 may be incorporated to allow operation of the above mentioned different coil configurations.

In use, an operator would connect probe 11 to a standard eddy current inspection unit with proper electrical conductors between connector 51 and the inspection unit. Next, to search for a crack under a chosen raised-head fastener, the operator would place probe 11 over the chosen raised-head fastener 35 and lower member 39 down in a manner such that the head of the chosen raised-head fastener 35 is substantially within the interior void of probe 11 as defined by inner wall 43 and such that bottom face 47 of member 39 substantially abuts upper sheet top surface 23. After calibrating the inspection unit, the user will rotate probe 11 about centerline 37 of the a chosen raised-head fastener 35 while ensuring that bottom face 47 of member 39 remains substantially abutted to upper sheet top surface 23. If the probe detects a crack, a crack signature will appear on a display screen of the inspection unit. While the above described use of probe 11 is described as a manually operated procedure, it will be appreciated that rotation of probe 11 and detection of cracks may be automated through the use of motors, computers, and/or other automation devices. For example, probe 11 may be robotically controlled to inspect for cracks at one or more fasteners 35 while crack identification is performed by a computer adapted for interpreting the signals received by the inspection unit. Of course any such automation may log or otherwise record crack detection results for later retrieval.

As explained above, probe 11 is well suited for crack detection in single wall and multi-layered aerospace structural members secured using raised-head fasteners. Probe 11 is adapted for detecting cracks under the fastener 35 head where the cracks have a thickness of up to about 0.080 inches and where crack thickness is defined as the distance from the edge of a hole in a metal sheet and extending radially outward from the centerline of the hole. Probe 11 is adapted for being driven by an oscillatory signal having a frequency of about 1 kHz to about 100 kHz. Of course, like other eddy current probes, probe 11 is driven at higher frequencies to more accurately detect cracks near upper sheet top surface 23. Similarly, probe 11 is driven at lower frequencies to more accurately detect cracks near lower sheet bottom surface 29.

Figure 4:
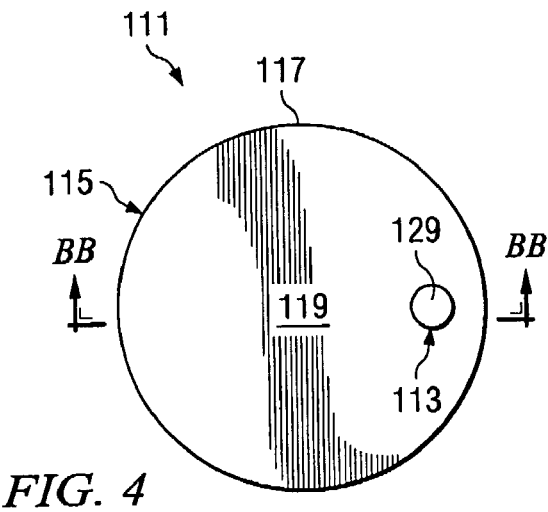
FIG. 4 is a top view of the preferred embodiment of a probe according to the present invention.
Figure 5:
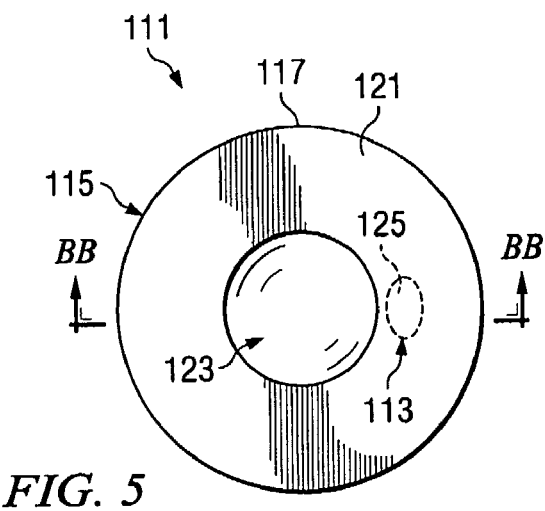
FIG. 5 is a bottom view of the probe of FIG. 4.
Figure 6:
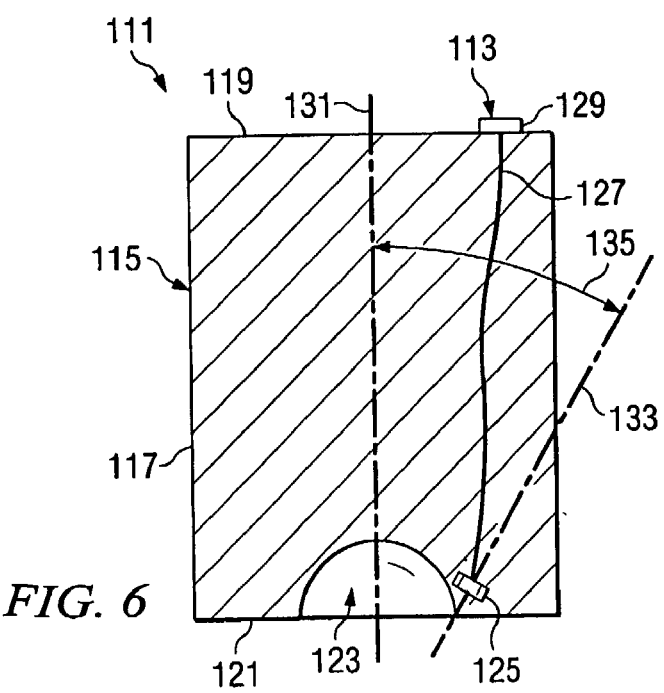
FIG. 6 is an enlarged sectional side view of the probe of FIG. 4.

Referring now to FIGS. 4-6 in the drawings, the preferred embodiment of a probe according to the present invention is illustrated. FIG. 4 is a top view. FIG. 3 is a bottom view. FIG. 3 is an enlarged side view of a cross-section taken at cutting line BB of FIG. 4 and viewed in the direction of the arrows connected to cutting line BB. Probe 111 comprises an eddy current coil system 113 and a support means 115 for supporting coil system 113. Eddy current coil system 113 is substantially similar in form, function, location, and construction to eddy current coil system 13. Support means 115 is substantially a solid cylinder having eddy current coil system 113 embedded within the cylinder structure. It will be appreciated that in other embodiments of the present invention, the support means may be shaped differently. Support means 115 comprises an outer wall 117, a top face 119, a bottom face 121, and a substantially concave receptacle 123 for receiving the head of a raised-head fastener 35 (see FIGS. 1-3). Coil system 113 comprises an eddy current coil 125 substantially similar to coil 31, a conductor 127 substantially similar to conductor 49, and a connector 129 substantially similar to connector 51 located on top face 119. Receptacle 123 is especially well suited for receiving the smooth heads of raised-head fasteners 35 and in particular, rivets having uniform and smooth heads. Receptacle 123 may be sized and shaped to accommodate reception of a myriad of rivet heads. Support means 115 comprises a support means centerline 131. Coil 125 is oriented such that a coil centerline 133 rests at an angle 135 of about 23 degrees from support means centerline 131.

Use of probe 111 is substantially similar to use of probe 11. During use of probe 111, an operator should ensure that bottom face 121 is substantially abutted to upper sheet top surface 23. Opportunity for inadvertent removal of bottom face 121 from upper sheet top surface 23 during use is reduced for use of probe 111 as compared to probe 11 since probe 111 provides more surface area contact between support means 115 and the head of a raised-head fastener 35 than the amount of surface area contact provided between support means 15 and the head of a raised-head fastener 35. Consequently, probe 111 may wobble less and provide more accurate crack detection than probe 11 if probe 11 is wobbled during use.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description.

The invention claimed is:

1. An eddy current probe, comprising:
    an eddy current coil having a coil centerline; and
    a support means having a body, the body comprising:
        an upper surface;
        a lower surface; and
        an inner void space having a centerline, the void space being disposed within the body, the void space extending from the upper surface to the lower surface of the body;
        wherein the void space is adapted for receiving a head of a raised-head fastener such that the centerline of the raised-head fastener aligns coaxially with the centerline of the void space;
    wherein the eddy current coil is disposed within the body of the support means; and
    wherein the centerline of the eddy current coil is oriented at an angular displacement relative to the centerline of the void space.

2. The eddy current probe according to claim 1, wherein the inner void space has a tubular shape for receiving the head of a raised-head fastener.

3. The eddy current probe according to claim 1, wherein the support means comprises a cylindrical member having a concave receptacle for receiving the head of a raised-head fastener.

4. The eddy current probe according to claim 1, wherein the selected angular displacement is maintained as the support means is rotated about the raised-head fastener centerline.

5. The eddy current probe according to claim 1, wherein the selected angular displacement is about 23 degrees.

6. The eddy current probe according to claim 1, wherein the coil is adapted for operation at a frequency of about 1 kHz to about 100 kHz.

7. A method of detecting cracks in metal below a head of a raised-head fastener, comprising the steps of:
    providing an eddy current coil according to claim 1,
    orienting the coil to a selected non-zero angle incident to a top surface of an upper sheet,
    electrically exiting the coil with an eddy current inspection unit,
    introducing an eddy current into a portion of metal below a head of a raised-head fastener,
    moving the coil along a perimeter of the head of the raised-head fastener, and
    identifying crack signatures displayed by the eddy current inspection unit.

8. The method of detecting cracks according to claim 7, wherein the movement of the coil along the perimeter is performed by a machine.

9. The method of detecting cracks according to claim 7, wherein the coil is exited with an electrical signal of about 1 kHz to about 100 kHz.

10. The method of detecting cracks according to claim 7, wherein the identification of crack signatures is performed by a computer.

11. An eddy current probe, comprising:
    an eddy current coil having a coil centerline;
    a support means having a body, the body comprising:
        an upper surface;
        a lower surface; and
        an inner void space having a centerline, the void space being disposed within the body, the void space extending from the upper surface to the lower surface of the body;
        wherein the void space is adapted for receiving a head of a raised-head fastener such that the centerline of the raised-head fastener aligns coaxially with the centerline of the void space;
    wherein the eddy current coil is disposed within the body of the support means;
    wherein the centerline of the eddy current coil is oriented at an angular displacement relative to the centerline of the void space; and
    wherein the coil centerline is maintained at a selected non-zero angle incident to a top surface of an upper sheet and such that an eddy current produced by the coil is introduced to a portion of the upper sheet directly below a head of a raised-head fastener.

12. The eddy current probe according to claim 11, wherein the coil is an absolute type eddy current coil.

13. The eddy current probe according to claim 11, wherein the coil is a differential type eddy current coil.

14. The eddy current probe according to claim 11, wherein the coil is a reflection type eddy current coil.

15. The eddy current probe according to claim 11, wherein the selected non-zero angle is about 23 degrees.

16. The eddy current probe according to claim 11, wherein the coil is adapted for operation at a frequency of about 1 kHz to about 100 kHz.

17. The eddy current probe according to claim 11, wherein the support means is adapted to at least partially receive the head of the raised-head fastener.

18. The eddy current probe according to claim 11, wherein the coil is oriented with respect to the head of the raised-head fastener such that eddy currents passing through the head of the raised-head fastener provide additional crack detection capability.

19. The eddy current probe according to claim 11, wherein the coil is oriented with respect to the head of the raised-head fastener such that eddy currents passing through the head of the raised-head fastener provide no additional crack detection capability.

* * * * *